(12) United States Patent
Gruber (10) Patent No.: US 7,487,682 B2
(45) Date of Patent: Feb. 10, 2009

(54) MEASURING CELL AS WELL AS CONSTRUCTING METHODS FOR A MEASURING CELL AND MEASURING APPARATUS WITH A MOUNT FOR SUCH A MEASURING CELL

(76) Inventor: Markus Gruber, Dellstrasse 47, D-52072 Aachen (DE)

( * ) Notice: Subject to any disclaimer, the term of this patent is extended or adjusted under 35 U.S.C. 154(b) by 0 days.

(21) Appl. No.: 11/579,209

(22) PCT Filed: Apr. 27, 2005

(86) PCT No.: PCT/DE2005/000783

§ 371 (c)(1),
(2), (4) Date: Dec. 1, 2006

(87) PCT Pub. No.: WO2005/106442

PCT Pub. Date: Nov. 10, 2005

(65) Prior Publication Data

US 2007/0220970 A1    Sep. 27, 2007

(30) Foreign Application Priority Data

Apr. 30, 2004  (DE) ................ 10 2004 021 237
Aug. 26, 2004  (DE) ................ 10 2004 041 595

(51) Int. Cl.
*G01L 9/12* (2006.01)
(52) U.S. Cl. ...................................... 73/718
(58) Field of Classification Search ........... 73/58, 73/31.06, 718
See application file for complete search history.

(56) References Cited

U.S. PATENT DOCUMENTS

| 4,580,439 | A | 4/1986 | Manaka |
| 6,254,827 | B1 | 7/2001 | Ackley et al. |
| 6,987,312 | B2 | 1/2006 | Theuss |
| 2004/0016297 | A1* | 1/2004 | Paul et al. ............. 73/580 |

FOREIGN PATENT DOCUMENTS

| DE | 44 42 396 A1 | 5/1996 |
| JP | 10132679 | 5/1998 |
| JP | 11281614 | 10/1999 |
| WO | WO 03/067657 | 8/2003 |
| WO | WO 2005/121769 | 12/2005 |

OTHER PUBLICATIONS

Guo-Wei Xiao et al., "A pressure sensor using flip-chip on low-cost flexible substrate." 2001 Proceeding 51st, Electronic Components and Technology Conference. ECTC 2001, Orlando, FL, May 29, 2001, Proceedings of the Electronic Components and Technology Conference, New York, NY: IEEE, US, vol. CONF. 51, May 29, 2001, pp. 750-754, XP010547674.

* cited by examiner

*Primary Examiner*—Jewel Thompson
(74) *Attorney, Agent, or Firm*—Collard & Roe, P.C.

(57) ABSTRACT

The invention relates to a measuring cell, comprising a support and a sensor, whereby a measuring chamber is arranged between the support and the sensor and the sensor is arranged on the support by means of individual material deposits provided between the support and the sensor. Said material deposits are preferably gold bumps.

17 Claims, 3 Drawing Sheets

MEASURING CELL AS WELL AS CONSTRUCTING METHODS FOR A MEASURING CELL AND MEASURING APPARATUS WITH A MOUNT FOR SUCH A MEASURING CELL

CROSS REFERENCE TO RELATED APPLICATIONS

Applicant claims priority under 35 U.S.C. 119 of German application Ser. No. 10 2004 021 237.6 filed Apr. 30, 2004; and German application Ser. No. 10 2004 041 595.1 filed Aug. 26, 2004. Applicant also claims priority under 35 U.S.C. §365 of PCT/DE2005/000783 filed Apr. 27, 2005. The international application under PCT article 21(2) was not published in English.

The invention relates on one hand to a measuring cell comprising a support and a sensor, which features a measuring chamber arranged between the sensor and the support. On the other hand, the invention relates to a method for the construction of such a cell with a measuring chamber on which a sensor is arranged on a support. Furthermore, the invention relates also to a measuring apparatus with a mount for such a measuring cell mentioned above.

Especially for biochemical, chemical or pharmaceutical analytics, measuring cells are known that are designed and suitable to analyze small quantities of sample media. For this, the measuring cells are equipped with a sensor, which for instance consists of a quartz crystal resonator, electrically connected with two contact wires, that is usually clamped between two O-rings in that manner, that a measuring chamber is formed, that is bordered at least on one side directly by the quartz crystal resonator. On the quartz crystal resonator's surface, a ligand may be immobilized that has the ability to specifically bind or capture an analyte present in the sample media. The binding of the analyte causes the quartz crystal resonator to change the resonance frequency which may be used to proof the presence of the analyte in the sample media. This technique is commonly known as quartz-crystal-microbalance sensors (QCM sensors) or quartz-crystal-resonance sensors (QCRS). These sensors are successfully in use since a couple of years.

The volume of the sample media that has to be analyzed by the measuring cell, is defined by the volume of measuring chamber which is bordered by the o-rings, the quartz crystal resonator and the support, on which one of the O-rings is arranged directly. Current designs of such conventional measuring chambers feature a volume of about 50 to 200 µl. The disadvantage of such big chamber volumes for chemical, biochemical or pharmaceutical analytics is, that the required quantity of sample media to fill the chamber in order to allow a reliable analytical result with current techniques is too big. In many cases only limited quantities of sample media are available.

Furthermore, current measuring cells bear the risk that the thin and fragile quartz-crystal resonators get damaged due to mechanical stress applied to them during the assembly of the measuring cell. Moreover, the usage of tools like tweezers is inevitable when handling the quartz crystal resonators, thus the risk of damaging the fragile sensors increases further.

So as to avoid the above mentioned disadvantages, the document US 2004/0016297 A1 states that the sensors or rather the quartz crystal resonators are glued into ring-shaped plastic mounts, in order to reduce the risk of sensor damage and to reduce the volume of sample media.

The objective of the invention presented herein intends a further miniaturization of recent measuring cells and their measuring chambers.

This objective of the invention is achieved by a measuring cell consisting of a support and a sensor, forming a measuring chamber between the sensor and the support whereby the sensor is arranged on the support by individual material deposits located between the sensor and support.

Due to such an assembly, the measuring cell and the associated measuring chamber presented herein can be constructed in a particularly simple design, allowing miniaturization to provide a measuring chamber with a very low volume.

In this context, the objective of the invention is also achieved by a fabrication method of a measuring cell with a measuring chamber, whereas a sensor is superimposed on a support and where the sensor is fixed on the support by individual material deposits.

Due to the fact, that the sensor is fixed by individual material deposits on the support, other components or component assemblies, as required in state-of-art designs, are no longer necessary to provide a linkage between the sensor and the support.

The objective of the invention is implemented by a fabrication procedure for a measuring cell with a measuring chamber, which arranges a sensor of the measuring cell onto a support of the measuring cell using a flip-chip process. Due to that procedure, tools like tweezers or such are no longer required for sensor handling and thus obsolete.

It is particularly beneficial, if the material deposits are applied onto the support before the sensor is applied on the support. Thus, the sensor is set easily on top of the material deposits, so that the sensor and the support establishes a compact and fixed unit.

The measuring chamber of the measuring cell can be established conveniently, if the sensor is attached spaced to the support in such a way, as a measuring chamber is formed between the sensor and the support.

An advantage of the above described fabrication procedure is, that especially material deposits that are applied to the support in the flip-chip bonding process, for instance are small metal spheres, serve both, as spacer between the sensor and the support, and as an electrical contact to the sensor at least for the sensors surface facing to the support.

Since, the usage of tweezers or similar tools for handling and inserting the sensors into a mount is no longer necessary, it is beneficially possible, to use considerably thinner sensors for the fabrication of a measuring cell. The usage of these thinner sensors enables more precise measurements with the measuring cell presented herein, thus resulting in an improved analysis of the sample media.

It is further advantageous, if the material deposits are consisting of bumps attached onto the support using a bonding process. Such bumps are already known from different connection techniques, like tape-automated-bonding (TAB), chip-size-packaging (CSP) and the before mentioned bump- or flip-chip (FC) bonding.

Thus, such bumps, represent as material deposits that connect the sensor to the support of the measuring cell in a beneficial way without requiring other components or component assemblies to link the sensor and the support.

It is beneficial when the material deposits are used as spacer between the sensor and the support. In this way, the measuring chamber of the measuring cell is established in a particular simple way.

In order to establish an electrically conductive connection between the sensor and the support, it is useful, when the material deposits are electrically conductive.

It is understood that the material deposits meant for this invention may consist of varying materials that are suitable to establish a durable connection between the sensor and the support. For instance, the material deposits may consist of glue, adhesive, plastic or synthetics. In order to establish particular high-grade connections between the sensor and the support, it is beneficial if the material deposits contain gold, offering on the one hand very good electrical conductivity, while on the other hand affecting a sample media to be analyzed as little as possible. Furthermore the material gold has the characteristic to be very resistant and inert against all kinds of sample media.

As mentioned above, the material deposits position the sensor spaced from the support in such a way that the material deposits located near the sensor's outline prepare and ideally close the area between the sensor and the support to an enclosed measuring chamber. For this, it is favorable that the material deposits are arranged in the region near the sensor's outline between the sensor and the support. It shall be understood in this context, that there is no need that every individual material deposit is located completely between the sensor and the support. In fact in most cases it is sufficient, when the material deposit is partially located between the sensor and the support.

The material deposits may be provided conveniently, when they were deposited using a lithographically structured surface coating on the support. It shall be understood in this context, that also other techniques may be used to apply the material deposits to the surface of the support.

One version of the measuring cell is characterized by a support consists of a glass plate or slide. It shall be understood that the support may also consist of other materials as plastics or other substrates for circuit boards.

It is proposed, that the support is at least partially electrically conductive. A glass plate or glass slide may for instance be rendered electrically conductive by surface metallization and furthermore it may be used as a circuit board or conductor board by structuring this metal layer.

In order to transmit selectively directed signal information, it is advantageous, if the support features conducting paths. If the support has such conducting paths, the connection from the sensor to an interface circuit can be established in a particularly simple way.

To achieve access to the measuring chamber of the measuring cell presented herein, it is beneficial if there is an inlet and/or an outlet arranged on the support. In the case presented it has been shown favorable if the support features a single drill hole for the inlet and multiple, for example four drill holes for the outlet. Depending on the specific task other numerical rates between in- and outlets may be beneficial.

Advantageously, it is possible to arrange multiple sensors and/or a sensor array on the support; thus it is possible to simultaneously analyze one sample media for multiple analytes or multiple sample medias for one analyte.

It shall be understood, that the measuring cell may be equipped with various sensor types. Especially in the field of chemical, biochemical or pharmaceutical analytics, it is advantageous, if the sensor consists of a piezoelectric or capacitive transducer. Amperometric or potentiometric sensors may also be used in association with the measuring cell presented herein.

Further useful applications of the measuring cell presented herein may also be found in medical diagnostics and in the determination of viscosities.

The measuring cell presented herein can be equipped with various types of piezoelectric crystals as a transducer. One beneficial option is, when the sensor is consisting of a quartz-crystal resonator.

One constructional advantageous option is a sensor that is equipped with electrodes on its surface facing the support and/or on its surface facing away from the support. These electrodes enable measurements at or near the sensor's surface. Furthermore, it is also possible to additionally provide one single or multiple electrodes on the support in the area of the measuring chamber. With these additional electrodes, two corresponding electrodes may be used to measure the electrical conductivity of the sample media or the electrical capacity which is influenced by the sample media. For the measurement of capacity, current or conductivity, these additional electrode(s) may be used as counter electrode(s) for the electrodes located on the sensor. The electrode(s) located in the region of the measuring chamber on the support may be used as reference electrodes for measuring electrical voltages or electrical potentials.

The electrical contacting of the sensor's surface facing away from the support is implemented using wires that for example may be fixed by soldering or bonding. Such wires do not significantly complicate the construction of the measuring cell and furthermore, they do not negatively impact the volume of the measuring chamber since they are arranged outside the measuring chamber.

With the measuring cell presented herein provides sufficiently precise measurement results, if the sensor has a diameter of less than 20 mm, preferably of less than 15 mm. It is not important, whether the sensor is a circular shaped disk or a rectangular shaped disk.

In order to further reduce the amount of sample media required for an analysis, it is beneficial if the measuring chamber has a volume of less than 20 µl, preferably less than 10 µl. As mentioned at the beginning of this document, conventional measuring chambers have significantly higher volumes, thus considerably more sample medium is required to achieve a sufficiently precise result.

A combination with a diameter of 14 mm for instance, a measurement chamber with a volume of less than 8 µl can be achieved without negatively affecting the accuracy of measurement.

With the previously described measuring cell design and the described method for the construction of the measuring cell, it is possible to arrange the sensor particularly close to and opposite to the support, that a measuring cell with a particular flat measuring chamber can be obtained.

The measuring chamber can be provided in a constructional convenient way, if the material deposits are located between the sensor and the support near the sensor's outline.

The measuring chamber can be closed particularly leak-proof in the area between the sensor and the support, if the measuring chamber is sealed by an additional sealant between the sensor and the support. Preferably this sealant is applied in the region near the sensor's outline.

Due to the electrically conductive material deposits, additional electrical contacts can be omitted beneficially. This favors further reduction of the measuring cell dimensions and especially of the dimensions of the measuring chamber.

The objective of the invention is also achieved by a measuring apparatus receiving a measuring cell according to the previously mentioned requirements.

The measuring apparatus is easy to handle, if it possesses a sandwich-like structure. On one hand, the sandwich construction allows cost-effective manufacturing of the individual components and/or component assemblies. On the other hand it allows easy insertion of the measuring cell into the measuring apparatus.

It is favorable for this purpose, if the measuring apparatus is a housing that consists of several parts.

In order to reliably arrange the measuring cell in the measuring apparatus, it is favorable if the measuring apparatus features a mount for the measuring cell which preferably is demountable from the measuring apparatus.

In order to allow the sample media easy access to the measuring cell mounted in a measuring apparatus it is advantageous if the measuring apparatus has a fluidic block comprising an inflow and an outflow for the sample media. Using the inflow and outflow, the measuring chamber of the measuring cell is constructional easy accessible. It shall be understood, that such inflow and outflow capabilities may also be located in other parts or components of the measuring apparatus.

Beside the bottom layer, which closes the apparatus at its lower end, it is beneficial, when the measuring apparatus has a top cover with a circuit board containing interface-circuits and spring contacts for the automated contacting of the measuring cell to the circuit board.

The housing in several parts may be held together by various joining techniques. Rubber-like rings or metal springs used as clamping tools are a particular advantageous way to hold the measuring apparatus together.

It shall be understood, that sealings between all individual components may be used in order to improve tightness between these components.

Further advantages, objectives, and properties of the invention presented herein are described in the following explanations with reference to the accompanying drawings depicting an example of a measuring cell and a measuring apparatus The accompanying drawings show FIG. 1 a schematic longitudinal section of the measuring cell, FIG. 2 a schematic top view of the measuring cell shown in FIG. 1, FIG. 3 a schematic perspective view of a measuring apparatus in sandwich construction with an integrated measuring cell, and FIG. 4 a schematic top view of an alternative measuring cell.

Figure 1:
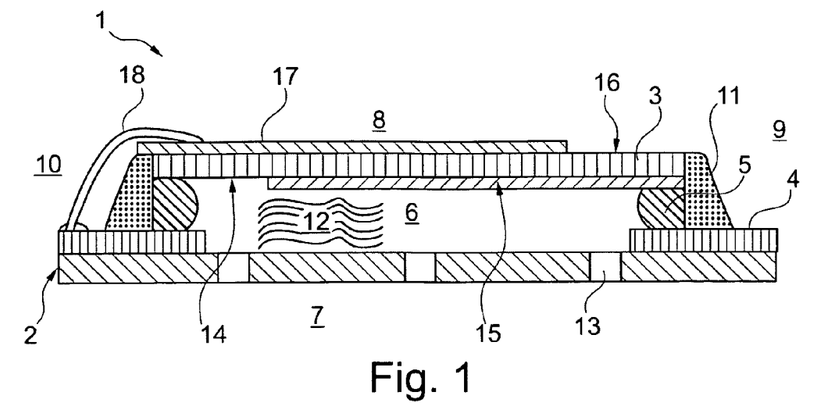
Figure 2:
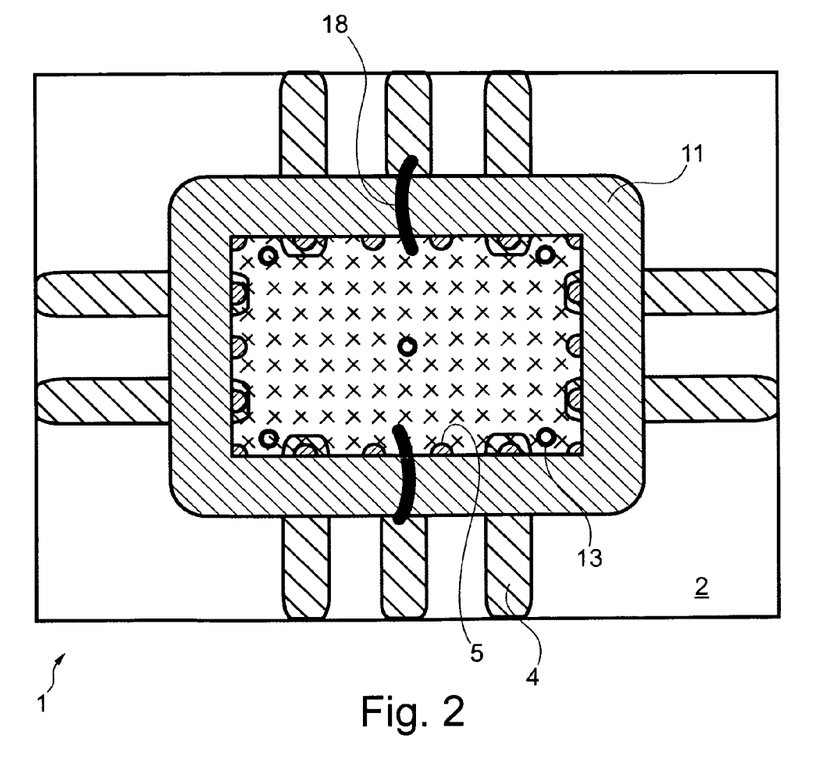

The measuring cell 1 shown in FIGS. 1 and 2 comprises a support 2 consisting of a glass plate and a sensor 3. The support 2 is covered single sided, in the example presented on its side facing towards the sensor 3, with conducting paths 4. A plurality of bumps 5 (numbered only exemplarily here) are applied between the sensor 3 and the support 2. Preferably, the bumps 5 are located in the area of the sensor's (3) outline in order to leave at least a part of the area between the sensor 3 and the support 2 vacant of material.

By means of the bumps 5, the sensor 3 is connected electrically to the support 2 and thus to the conducting paths 4 of the support 2, and additionally it is arranged spaced on the support 2 and thus forming a measuring chamber 6 between the sensor 3 and the support 2. The measuring chamber 6 presented is circumscribed by the bottom part 7 of the measuring cell 1 by the support 2, by the upper side 8 of the measuring cell 1 by the sensor 3 and both, on the right side 9 and on the left side 10 of the measuring cell 1 by multiple bumps 5, that may be—if applicable—fused together.

In order to increase the tightness of the measuring chamber 6 in the area where the bumps 5 are located, the measuring chamber 6 is additionally sealed in this area by a sealant 11 which is applied around the sensor's 3 outline. In this design example, the sealant 11 has the mere function to seal the gap and not to act as a glue to further fix the sensor 3 on the support 2. This fixing, that assures reliable attachment of the sensor 3 on the support 2, is provided in this design example essentially by the multitude of bumps 5.

To enable access of the sample media 12 into the measuring chamber 6, the support 2 features drill holes 13 (numbered only exemplarily here) that are used to achieve an inflow respectively an outflow for the sample media 12 into or out from the measuring chamber 6.

The sensor 3 features on its surface 14 facing towards the support 2 first electrodes 15 used for the immobilization of various biomolecules (not shown in the drawing) like antibodies, DNA, or receptors of the sample media. For the contacting between the surface 16 of the sensor 3 facing away from the support 2 and the conductive paths 4 on the support 2, the measuring cell 1 is equipped with contact wires 18, which are used establish the electrical connection between the upper electrode(s) 17 and the conducting paths 4.

Since the sensor 3 is mounted on the support 2 through a plurality of bumps 5, the distance between the sensor 3 and the support 2 can be kept short because no other additional components or component assemblies are required to fix the sensor 3 to the support 2. Thus, the measuring cell 1 has a simple and clearly arranged configuration, which enables simple and cost-effective manufacturing for the measuring cell 1. Due to the electrical conductivity of the bumps 5, an electrically conductive connection from the sensor 3 and/or the electrodes 15 of the sensor 3 to the support 2 can be established in a constructionally particular simple way, without requiring electrical conductive wires between the electrodes 15 and the conducting paths 4.

Figure 3:
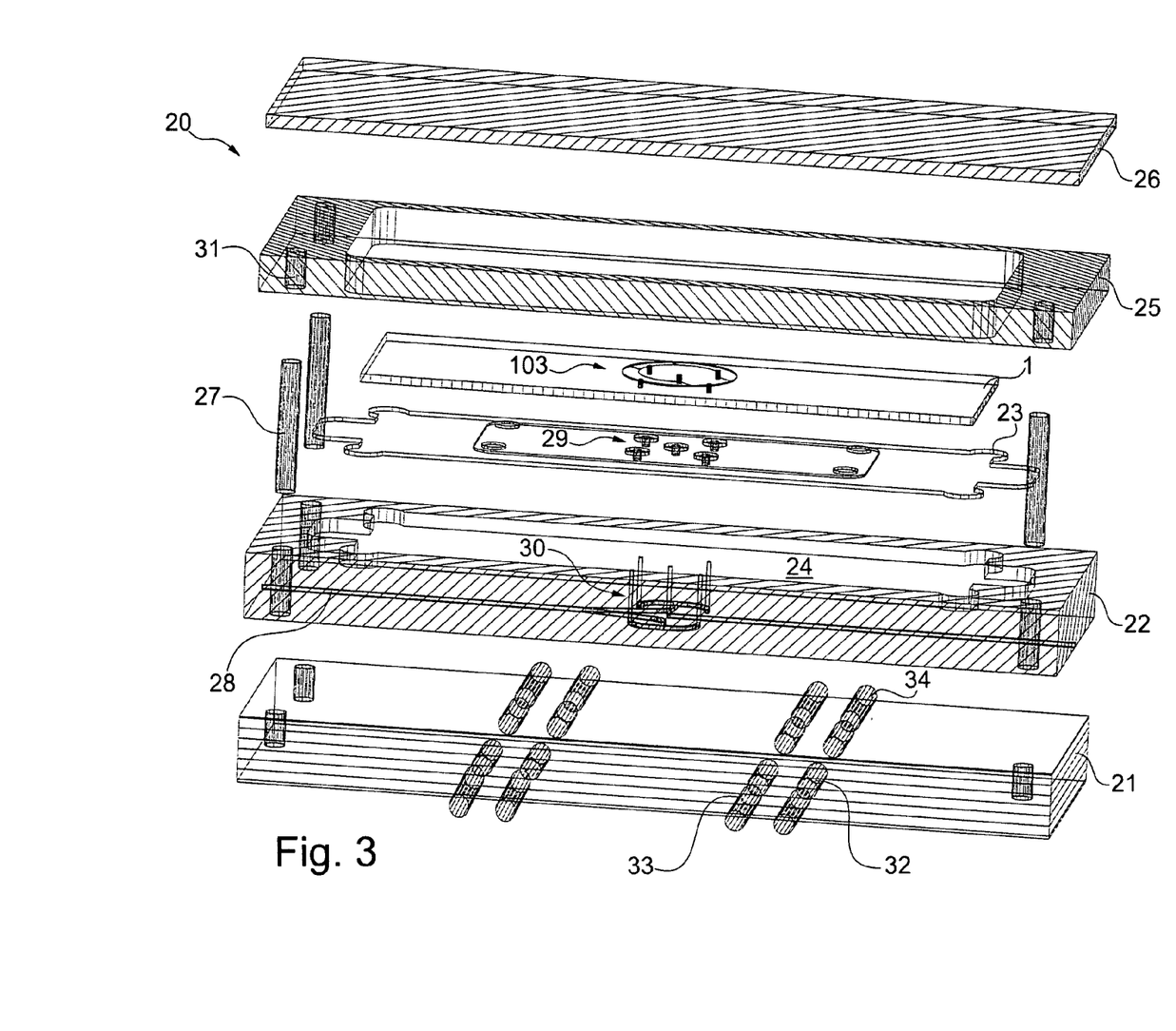

In order to load the measuring cell 1 fast and effectively with a sample medium 12, the multi-part measuring apparatus 20 shown in FIG. 3 is particularly suitable. The measuring apparatus 20 essentially is composed of a bottom plate 21, a fluidic block 22, an elastic sealing 23, a mount 24 for the measuring cell 1, a spacer 25, a top cover 26, as well as a plurality of guide pins 27. In the example shown here, the mount 24 for the measuring cell 1 is integrated into the fluidic block 22.

The bottom plate 21 completes the measuring apparatus 20 at its bottom end. The fluidic block 22 is attached to the bottom plate 21. The fluidic block 22 exhibits a channel system 28 which is corresponding with the drill holes 13 of the measuring cell 1. By this channel system 28, the measurement chamber 6 is filled with, respectively emptied from the sample media 12. The elastic sealing 23, which features sealed fittings 29 that enable it to establish a reliable connection between the channel system 28 of the measuring apparatus 20 and the drill holes 13 of the measuring cell 1, is inserted into the fluidic block 22.

The elastic sealing 23 is made in the example shown here of a silicone elastomer. Other materials such as rubber, rubber-like or silicone elastomer-similar materials like poly-dim-ethyl-siloxane (PDMS) may also be used for this purpose.

The sealing 23 is applied on the fluidic block 22 and afterwards the measuring cell 1 is inserted into the mount 24 on the fluidic block 22. The measuring cell 1 is arranged in such a way in the mount 24, that the drill holes 13 of the measuring cell 1 interact as a sealing with the rising pipes 30 of the channel system 28.

On the upper side, the measuring apparatus 20 is terminated and closed by the top cover 26. The top cover 26 is spaced from the fluidic block 22 by the spacer 25.

In order to simplify the assembly and the adjustment of the components, especially the bottom plate 21, the fluidic block 22 and the spacer 25 feature drill holes for the insertion of guide pins 27. By this procedure, the individual components of the measuring apparatus 20 are adjusted in the correct position. This simplifies the assembly of the measuring apparatus 20 significantly.

The bottom plate 21 furthermore shows a plurality of horizontal holes 32 in which horizontal pins 33 and 34 may be inserted. The horizontal pins 33, 34 mounted in the bottom plate 21 are used for the attachment of a rubber strip (not shown in the drawing for clarity) which is spanned beginning at the horizontal pins 33 over the top cover 26 of the assembled measuring apparatus 20 to the horizontal pins 34. In this design example, the horizontal pins 34 are located at the bottom plate 21, opposite to the horizontal pins 33.

The measuring apparatus 20 presented herein is especially characterized by a simple sandwich-construction which can be assembled and disassembled easily. As compared with other similar state-of-the-art devices there are no tools required, neither for the insertion of the measuring cell 1, nor for the assembly or disassembly of the measuring apparatus 20, since all components only need to be plugged together in a constructional simple way. Due to the elastic rubber strip, which is spanned from the horizontal pins 33 over the top cover 26 back to the horizontal pins 34, a sufficient and reliable facility is created to close the measuring apparatus 20 and to hold its components together.

The top cover 26 is also used as a circuit board which features interface electronics and spring contacts (both not shown in the drawing). The spring contacts serve to establish automatically the connection between the interface electronics and the measuring cell 1 when the measuring apparatus 20 is assembled and closed.

Alternatively, the fluidic block 22 can be coupled permanently to the bottom plate 21 by means of adhesive bonding, welding or another coupling technique, so that the fluidic block 22 and the bottom plate 21 form an unseparable and fixed unit of the measuring apparatus 20. It shall be understood, that the bottom plate 21 and the fluidic block 22 may also be fabricated as a single piece, so that it is no longer necessary to use a coupling technique for coupling the bottom plate 21 to the fluidic block 22.

Figure 4:
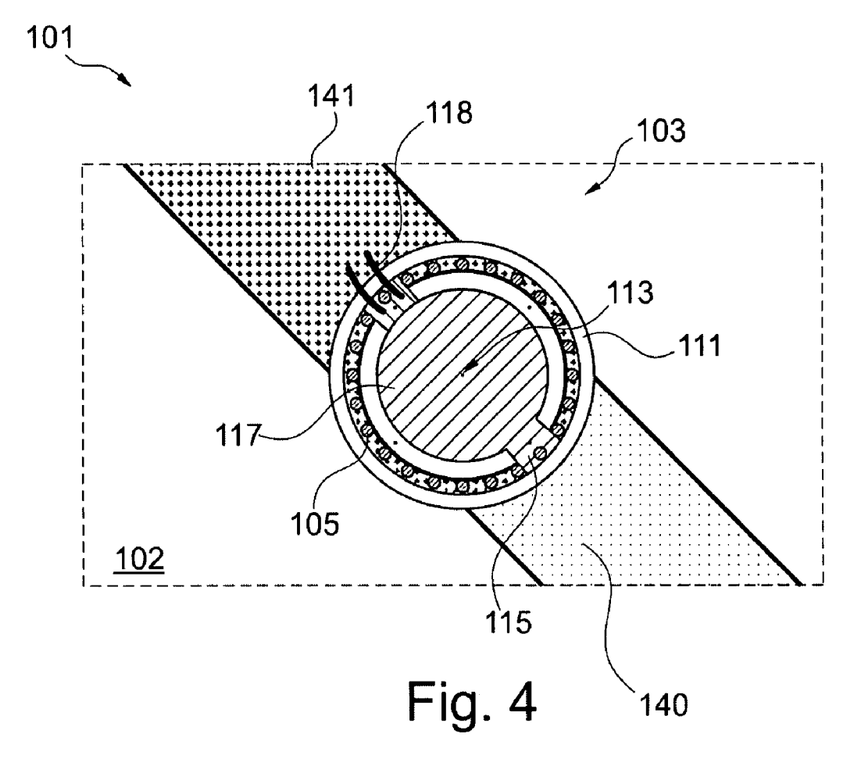

The measuring cell 101 shown in FIG. 4 exhibits a support 102 made of glass. A piezoelectric sensor 103 is arranged on the support 102. Furthermore, the support 102 shows a first electrical conducting path 140 and a second electrical conducting path 141. The sensor 103 is fixed by a plurality of gold-bumps 105 arranged concentrically in the region of the sensor's outline on the support 102. The gold-bumps 105 enable on one hand, a very good contact between the first conducting path 140 and the sensor's surface facing to the support and the electrodes 115 of the sensor 103 that are located there facing towards the support 2. On the other hand the gold-bumps 105 fix the sensor 103 spaced on the support 102 in such a way that a measuring chamber is established in which a sample media can be introduced. The sample media passes through holes 113 (here numbered only exemplarily) provided on the support 102 into the measuring chamber of the measuring cell 101.

The second conducting path 142 is electrically connected by connection wires 118 (numbered only exemplarily) to an electrode 117 of the sensor 103 which is located on the side of the sensor 103 facing away from the support 102.

In order to seal the measuring chamber completely in the region at the sensor's 103 border, a sealant 111 is provided between the support 102 and the sensor 103. While the measuring chamber is defined at the upper side by the sensor 103, at the bottom by the support 102, while the sealant 111 circumvents the measuring chamber 111 laterally.

The electrode(s) 115 of the sensor 103 facing towards the support 102 are chemically modified or functionalized in shown example in such a way, that a ligand (not shown in the drawing) can be immobilized on these electrode(s) 115. The presence of an analyte (not shown in the drawing) in a sample media is verified by means of the ligand.

It shall be understood, that the examples shown in the drawings do not restrict the invention presented herein in any way, since they are only intended as design examples. An expert recognizes, that the measuring cells and the measuring apparatus shown in the drawings may vary in shape and design.

The invention claimed is:

1. A measuring cell comprising:
   (a) a support;
   (b) at least one sensor;
   (c) a leak-proof measuring chamber disposed in a gap between the support and the at least one sensor;
   (d) at least one inlet in communication with the measuring chamber, wherein the at least one inlet allows an inflow of a sample media into the measuring chamber;
   (e) at least one outlet in communication with the measuring chamber, wherein the at least one outlet allows an outflow of the sample media from the measuring chamber; and
   (f) a plurality of individual material deposits serving as spacers for arranging the at least one sensor spaced apart from the support.

2. The measuring cell according to claim 1, wherein said material deposits are electrically conductive.

3. The measuring cell according to claim 1, wherein said material deposits comprise bumps applied on the support using a bonding procedure.

4. The measuring cell according to claim 1, wherein said material deposits contain gold.

5. The measuring cell according to claim 1, wherein said material deposits were applied on a lithographically structured surface coating of the support.

6. The measuring cell according to claim 1, wherein said support comprises a glass plate or slide.

7. The measuring cell according to claim 1, wherein the measuring chamber is sealed in the area between the support and the sensor by a sealant.

8. The measuring cell according to claim 1, wherein said support is at least in parts electrically conductive.

9. The measuring cell according to claim 1, wherein said support comprises conducting paths.

10. The measuring cell according to claim 1, wherein at least one additional electrode is located in the region of the measuring cell on the support.

11. The measuring cell according to claim 1, wherein the sensor comprises electrodes on a side of the sensor facing towards the support and/or on a side of the sensor facing away from the support.

12. The measuring cell according to claim 1, wherein said at least one sensor comprises piezoelectrical material.

13. The measuring cell according to claim 1, further comprising an arrangement of electrodes on the at least one sensor and/or on the support which permit measurement of electrical capacities, voltages or conductivities.

14. The measuring cell according to claim 1, wherein said at least one sensor comprises an amperometric, a potentiometric or a capacitive transducer.

15. The measuring cell according to claim 1, wherein at least one additional electrode located on the support is used as a counter electrode when measuring the conductivity of a sample media or as reference electrode when the at least one sensor comprises a capacitive, an amperometric or a potentiometric transducer.

16. The measuring cell according to claim 1, wherein at least one electrode is chemically modified and/or functionalized and/or comprises immobilized receptor molecules.

17. The measuring cell according to claim 2, wherein said plurality of individual material deposits provide an electrical connection between the at least one sensor and the support.

* * * * *

UNITED STATES PATENT AND TRADEMARK OFFICE
CERTIFICATE OF CORRECTION

PATENT NO. : 7,487,682 B2
APPLICATION NO. : 11/579209
DATED : February 10, 2009
INVENTOR(S) : Gruber It is certified that error appears in the above-identified patent and that said Letters Patent is hereby corrected as shown below:

Title page, illustrative fig. 1 should be deleted and substitute therefore the attached title page consisting of the attached illustrative fig. 1.

In the Drawings

Figs. 1 and 4 are corrected as shown on the attached pages 3 and 4 of 4.

Signed and Sealed this

Twenty-second Day of December, 2009

David J. Kappos
*Director of the United States Patent and Trademark Office*

(12) United States Patent
Gruber (10) Patent No.: US 7,487,682 B2
(45) Date of Patent: Feb. 10, 2009

(54) MEASURING CELL AS WELL AS CONSTRUCTING METHODS FOR A MEASURING CELL AND MEASURING APPARATUS WITH A MOUNT FOR SUCH A MEASURING CELL

(76) Inventor: Markus Gruber, Dellstrasse 47, D-52072 Aachen (DE)

(*) Notice: Subject to any disclaimer, the term of this patent is extended or adjusted under 35 U.S.C. 154(b) by 0 days.

(21) Appl. No.: 11/579,209

(22) PCT Filed: Apr. 27, 2005

(86) PCT No.: PCT/DE2005/000783
§ 371 (c)(1),
(2), (4) Date: Dec. 1, 2006

(87) PCT Pub. No.: WO2005/106442
PCT Pub. Date: Nov. 10, 2005

(65) Prior Publication Data
US 2007/0220970 A1 Sep. 27, 2007

(30) Foreign Application Priority Data
Apr. 30, 2004 (DE) .................... 10 2004 021 237
Aug. 26, 2004 (DE) .................... 10 2004 041 595

(51) Int. Cl.
*G01L 9/12* (2006.01)
(52) U.S. Cl. .................................................. 73/718
(58) Field of Classification Search .................. 73/58, 73/31.06, 718
See application file for complete search history.

(56) References Cited

U.S. PATENT DOCUMENTS

| 4,580,439 A | 4/1986 | Manaka |
| 6,254,827 B1 | 7/2001 | Ackley et al. |
| 6,987,312 B2 | 1/2006 | Theuss |
| 2004/0016297 A1* | 1/2004 | Paul et al. ............... 73/580 |

FOREIGN PATENT DOCUMENTS

| DE | 44 42 396 A1 | 5/1996 |
| JP | 10132679 | 5/1998 |
| JP | 11281614 | 10/1999 |
| WO | WO 03/067657 | 8/2003 |
| WO | WO 2005/121769 | 12/2005 |

OTHER PUBLICATIONS

Guo-Wei Xiao et al., "A pressure sensor using flip-chip on low-cost flexible substrate." 2001 Proceeding 51st, Electronic Components and Technology Conference. ECTC 2001, Orlando, FL, May 29, 2001, Proceedings of the Electronic Components and Technology Conference, NewYork, NY: IEEE, US, vol. CONF. 51, May 29, 2001, pp. 750-754, XP010547674.

\* cited by examiner

Primary Examiner—Jewel Thompson
(74) Attorney, Agent, or Firm—Collard & Roe, P.C.

(57) ABSTRACT

The invention relates to a measuring cell, comprising a support and a sensor, whereby a measuring chamber is arranged between the support and the sensor and the sensor is arranged on the support by means of individual material deposits provided between the support and the sensor. Said material deposits are preferably gold bumps.

17 Claims, 3 Drawing Sheets

UNITED STATES PATENT AND TRADEMARK OFFICE
CERTIFICATE OF CORRECTION

PATENT NO. : 7,487,682 B2  Page 3 of 4
APPLICATION NO. : 11/579209
DATED : February 10, 2009
INVENTOR(S) : Gruber It is certified that error appears in the above-identified patent and that said Letters Patent is hereby corrected as shown below:

Please replace Fig. 1 with CORRECT Fig. 1 below:

Fig. 1

UNITED STATES PATENT AND TRADEMARK OFFICE
CERTIFICATE OF CORRECTION

PATENT NO. : 7,487,682 B2
APPLICATION NO. : 11/579209
DATED : February 10, 2009
INVENTOR(S) : Gruber It is certified that error appears in the above-identified patent and that said Letters Patent is hereby corrected as shown below:

Please replace Fig. 4 with CORRECT Fig. 4 below:

Fig. 4